US007970097B2

(12) United States Patent
Bruder et al.

(10) Patent No.: US 7,970,097 B2
(45) Date of Patent: Jun. 28, 2011

(54) METHOD FOR PRODUCING TOMOGRAPHIC IMAGES, CONTROL DEVICE, TOMOGRAPHY UNIT AND COMPUTER PROGRAM PRODUCT

(75) Inventors: Herbert Bruder, Höchstadt (DE); Thomas Flohr, Uehlfeld (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/458,806

(22) Filed: Jul. 23, 2009

(65) Prior Publication Data

US 2010/0027736 A1 Feb. 4, 2010

(30) Foreign Application Priority Data

Jul. 24, 2008 (DE) .......................... 10 2008 034 564

(51) Int. Cl.
*A61B 6/00* (2006.01)
(52) U.S. Cl. ............................................. 378/8; 378/19
(58) Field of Classification Search .................. 378/8, 19
See application file for complete search history.

(56) References Cited

U.S. PATENT DOCUMENTS

| | | | | |
|---|---|---|---|---|
| 2005/0058248 A1* | 3/2005 | Klingenbeck-Regn | ......... | 378/95 |
| 2006/0140337 A1* | 6/2006 | Miyazaki et al. | .................. | 378/8 |
| 2006/0188058 A1* | 8/2006 | Bruder | ............................... | 378/8 |
| 2006/0274878 A1* | 12/2006 | Hsieh et al. | ........................ | 378/8 |
| 2007/0030735 A1 | 2/2007 | Bruder et al. | | |
| 2007/0041490 A1* | 2/2007 | Jha et al. | ............................. | 378/8 |
| 2007/0053483 A1* | 3/2007 | Nagata et al. | ...................... | 378/8 |
| 2007/0116172 A1* | 5/2007 | Hsieh et al. | ........................ | 378/8 |
| 2008/0165919 A1 | 7/2008 | Bruder et al. | | |
| 2009/0310737 A1* | 12/2009 | Forthmann et al. | ................ | 378/8 |
| 2010/0040193 A1* | 2/2010 | Lessick | ............................. | 378/8 |

FOREIGN PATENT DOCUMENTS

| | | |
|---|---|---|
| DE | 102005036963 B3 | 2/2007 |
| DE | 102006060482 A1 | 6/2008 |

* cited by examiner

*Primary Examiner* — Edward J Glick
*Assistant Examiner* — Alexander H Taningco
(74) *Attorney, Agent, or Firm* — Harness, Dickey & Pierce, P.L.C.

(57) ABSTRACT

A method is disclosed for producing tomographic images relating to different movement phases of a periodically moving object with the use of a tomography unit that includes a recording system that is arranged rotatably about a z-axis of the tomography unit, the recording system including an X-ray tube to which a tube current can be applied and a detector (17, 18) for acquiring projections. In at least one embodiment, the recording system is initially positioned relative to the object at a first z-position, and projections are acquired from a multiplicity of different projection dimensions at this z-position, in a fashion triggered by a movement signal representing the movement of the object, projections relating to a first movement phase of the object being acquired in a prospectively defined first time window and projections relating to at least a second movement phase of the object being acquired in a prospectively defined second time window. In at least one embodiment, a modulation of the tube current is performed in such a way that different tube current values are set in the first and the second time window to attain a prescribable different signal-to-noise ratio in the produced images. The recording system is then positioned sequentially at further z-positions, and respectively corresponding projections are acquired there for the two movement phases until a prescribed examination area is scanned at the desired z-positions. Tomographic images are reconstructed in real time or subsequently on the basis of the obtained projections.

18 Claims, 3 Drawing Sheets

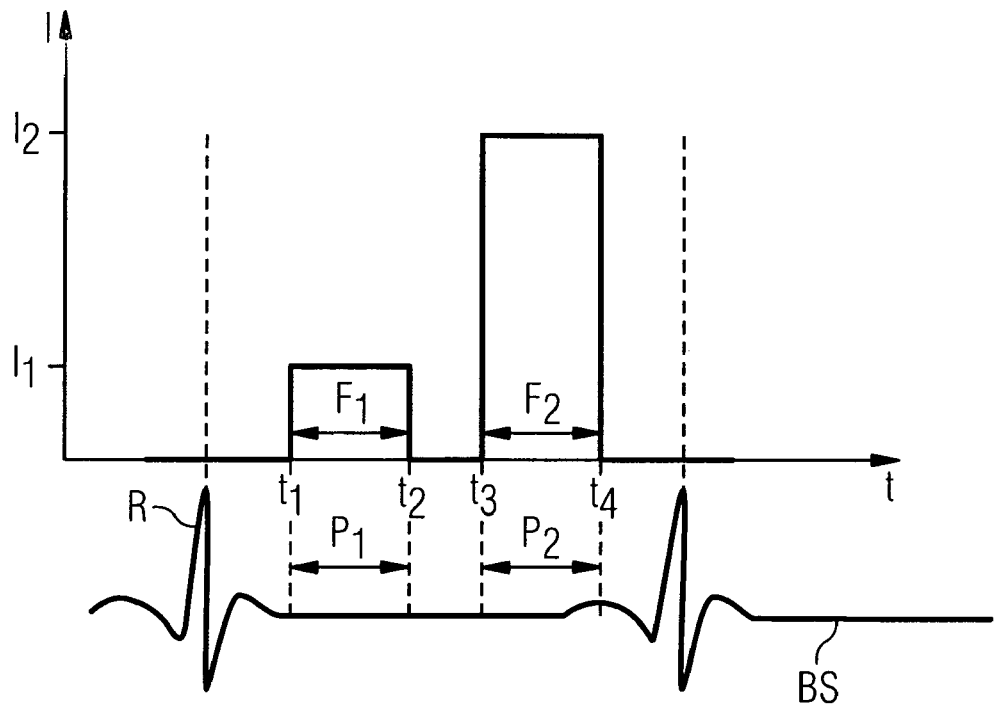
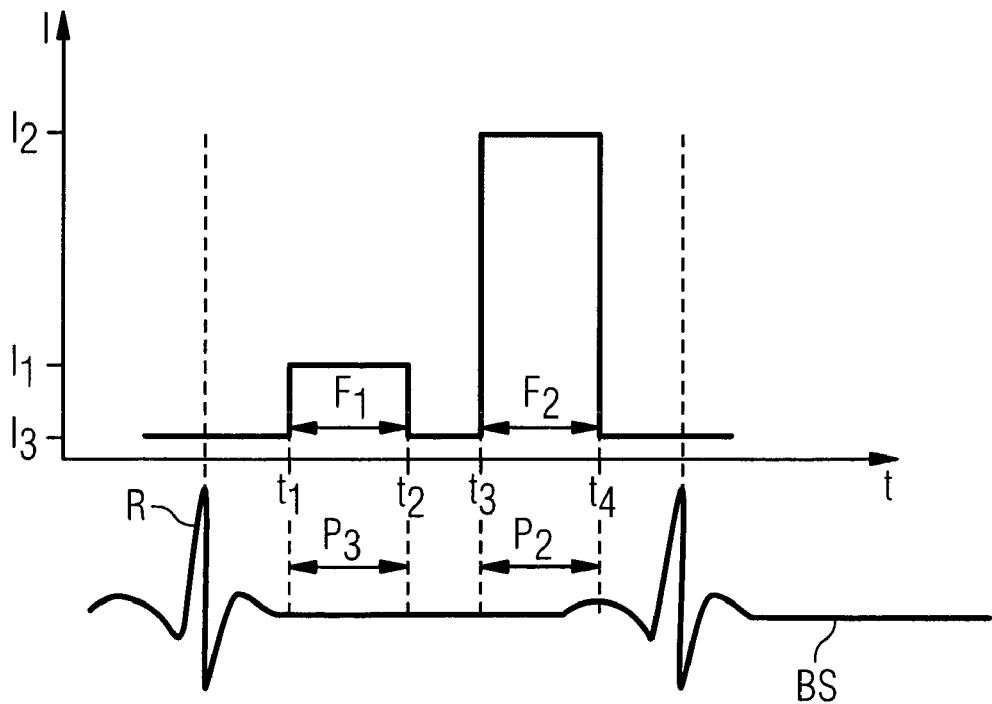

METHOD FOR PRODUCING TOMOGRAPHIC IMAGES, CONTROL DEVICE, TOMOGRAPHY UNIT AND COMPUTER PROGRAM PRODUCT

PRIORITY STATEMENT

The present application hereby claims priority under 35 U.S.C. §119 on German patent application number DE 10 2008 034 564.4 filed Jul. 24, 2008, the entire contents of which are hereby incorporated herein by reference.

FIELD

At least one embodiment of the invention generally relates to a method for producing tomographic images relating to different movement phases of a periodically moving object, in particular a cyclically moving organ of a patient or test subject, with the use of a tomography unit that comprises at least one recording system that is arranged rotatably about a z-axis of the tomography unit and has an X-ray tube to which a tube current can be applied, and a detector for acquiring projections. At least one embodiment of the invention further generally relates to a control device for such a tomography unit, a tomography unit with such a control device, and/or a computer program product for a programmable control device of a tomography unit.

BACKGROUND

Particularly in the case of medical imaging for the purpose of imaging the heart and the blood vessels near the heart, there is a general problem that as a consequence of the heartbeat, the examination area to be recorded is subject to a continuous periodic movement as a result of which tomographic images are comparable with one another only whenever they have been recorded in relation to the same phases of a cardiac cycle. This circumstance is problematic particularly in the case of computed tomography examinations in the case of which the tomographic images to be produced are calculated by back projection of a multiplicity of projections acquired from different projection angles. The back projection is generally successful and free from interference when the basic projections image a substantially identical phase of the cardiac cycle. A displacement, caused by cardiac arrhythmias, of the scanning with reference to the phase is expressed in movement artifacts in the resulting tomographic image.

In order to enable a reconstruction of a tomographic image representing the heart with small movement artifacts, projections can be obtained in relation to one and the same phase from a multiplicity of different projection directions by evaluating an ECG signal derived from the patient. There are two methods for ECG controlled acquisition of projections that can be distinguished in principle by approach.

One possibility resides in acquiring projections during the entire cyclic duration of the heart movement, and storing them together with the ECG signal. The reconstruction of a tomographic image is performed following on from the data acquisition, projections relating to defined phases retrospectively being selected using the ECG signal. One advantage of this method consists in that it is possible to display arbitrary movement phases of the heart by suitable selection of the data intervals. A precondition for such a retrospective gating in the case of the reconstruction of tomographic images is that the patient be irradiated during the entire scanning with a full X-ray dose, the result being the application of a substantially higher X-ray dose than necessary.

A further possibility resides in carrying out sequential scans triggered prospectively by the ECG in order to minimize the radiation dose during cardiac computed tomography. Such a method is described, for example, in DE 10 2006 060 482 A1. In the case of such sequential scanning, the recording system is moved relative to the examined object to various z-positions along the z-axis, and projections are respectively prepared at the relevant z-position, the time window in which the projections are produced being defined as a function of the ECG signal. For example, it is possible to define a specific time window by a starting point and an end point that are determined relative to a previously measured last R-wave in the ECG. The data recording is mostly performed in this case in an accurately defined time window in the area of the end diastole, in order to display the coronary vessels in a fashion free from movement.

For functional cardiac imaging, in particular for the purpose of determining the ejection fraction, that is to say the proportion of the blood volume ejected during the contraction of the heart to the total volume of the ventricle, there is additionally the need also to prepare an image in the phase of the maximum contraction, that is to say at the instant of the end systole.

SUMMARY

In at least one embodiment of the present invention, a method and a control device are disclosed for a tomography unit and a corresponding tomography unit to the effect that perfectly good tomographic images can be acquired with a low X-ray dose in different movement phases for a functional imaging.

An example method of at least one embodiment includes:

a) Initially, the recording system is positioned relative to the object in a first z-position along the z-axis.

b) Projections are then acquired from a multiplicity of different projection directions at this first z-position. In this case, it is preferred respectively to acquire so many projections that measured data are available for parallel projections over an angular interval of a total of at least 180° plus the system-dictated fine angle (and, if appropriate, also an additional angle of 30° relating to the overlaying between starting and final projections). In this case, in a fashion triggered by a movement signal, for example an ECG, representing the movement of the object, projections relating to a first movement phase of the object are acquired in a prospectively defined first time window and projections relating to at least a second movement phase of the object are acquired in a prospectively defined second time window and according to the invention a modulation of the tube current is performed in such a way that different values of the tube current are set in the first and the second time window in order to attain a prescribable different signal-to-noise ratio in the produced images.

c) Subsequently, in each case in a fashion analogous to method step a) the recording system is positioned sequentially at further z-positions along the z-axis relative to the object, and corresponding projections for at least the two movement phases are respectively acquired at the z-positions in accordance with method step b). These steps are repeated until a prescribed examination area which encompasses at least a prescribed part of the object to be examined, or even the entire object, if appropriate, is scanned at the desired z-positions.

d) Furthermore, a reconstruction of the tomographic images is performed for at least the two movement phases on the basis of the obtained projections. Such a reconstruction can be performed in real time, that is to say respectively during the carrying out of steps a) to c), or else subsequently when all the projections have been recorded.

It may be pointed out at this juncture that a movement phase is to be understood as any desired defined time interval within a movement cycle. Such a movement phase can be defined, for example, in the form of numerical values, for example a percentage or in time units, relative to a characteristic value in the movement signal. A typical example would be defining a time period in milliseconds after the last R-wave or before the estimated occurrence of the next R-wave in an ECG. However, it is likewise also possible to characterize a movement phase by a specific characteristic action within the movement signal, for example the area of the systole, the end systole, the diastole or the end diastole in the case of a heart movement.

The inventors have recognized that the applied X-ray dose for producing tomographic images relating to different movement phases can be further reduced when the scanning is carried out in accordance with a minimum image quality, required in order to answer a set of questions on which the respective examination is based, of the movement phase to be displayed. Thus, mostly different image features are viewed in the images, for example for later diagnostic purposes, it being possible to extract the image features with a different minimum image quality. Thus, for example, there is no need in the case of functional cardiac imaging to produce high quality tomographic images both in the end diastole and in the end systole. For example, it suffices to prepare an image with a very low noise in only one of the phases, generally the end diastole, displaying not only the ventricle, but also the coronary vessels in a fashion free from movement. Since the additional image of the end systole is still required only in order to determine the ejection fraction, for example, an image with relatively high image noise suffices for this purpose because, by contrast with the coronary vessels, the ventricle will also be detected even in the case of images with relatively high noise. It is therefore sensible to measure the recordings for this movement phase with a lesser dose.

Carrying out the measurement as a sequential measurement in accordance with at least one embodiment of the invention likewise contributes to the reduction of the dose. Thus, it would certainly be possible to carry out a functional evaluation in principle with the aid of a spiral scan, and it would be possible to modulate the X-ray current as a function of the ECG in an analogous way in order to reduce the X-ray dose. It is true that such a spiral scan is quicker overall, but it has the disadvantage that it is also necessary for the feed rate of the table, the so-called pitch, to be set prospectively. In this case, the pitch must be selected such that during the longest RR cycle of the ECG the feed is less than the detector width, otherwise gaps could occur in the scanned volume. Consequently, in the use of such a procedure—particularly if the heart rate fluctuates strongly during the scan—it is necessary to select the pitch to be smaller than optimum. This would lead to a considerable overlapping scanning of the volume that supplies only redundant data, and increases the dose of the examination. In the case of the inventive sequential scan, it is preferably possible simply to ensure that the acquired projections for adjacent z-positions border on one another, or otherwise overlap one another only slightly, in order nevertheless to scan the desired examination area without a gap.

In order to carry out at least one embodiment of the method, an inventive control device is required for a tomography unit, that has at least one recording system which is arranged rotatably about a z-axis and comprises an X-ray tube, to which an X-ray current can be applied, and a detector for acquiring projections, as well as a positioning device in order to position the recording system relative to an object to be examined at prescribed z-positions along the z-axis. The inventive control device requires an interface for acquiring a movement signal representing the movement of the object, an interface for driving the recording system, and an interface for driving the positioning device. In addition, the control device must be designed such that it drives the recording system and the positioning device in accordance with the movement signals acquired via the movement signal interface and in accordance with the prescribed method steps in order to produce tomographic images relating to different movement phases of a periodically moving object.

In addition to the customary recording system that can rotate about the z-axis, and to said positioning device, an inventive tomography unit of at least one embodiment requires such an inventive control device in order to position the recording system at prescribed z-positions along with z-axis relative to an object to be examined. Moreover, the tomography unit should also have an image computer unit that is designed such that it reconstructs tomographic images in a real time fashion or subsequently on the basis of the obtained projections.

The majority of the components for implementing at least one embodiment of the invention in a control device can be implemented entirely or partially in the form of software modules on a processor. In particular, for example, the interfaces can be designed as pure hardware components, but can also be implemented as software modules, for example when the data can be taken over from other components already implemented on the same unit, or must be transferred to another component only by using software. In particular, the interfaces can also comprise hardware and software components such as, for example, a standard hardware interface that is specially configured by software for the particular use.

At least one embodiment of the invention therefore also comprises a computer program product that can be loaded directly into a memory of a programmable control device of a tomography unit that has program code sections in order to execute all the steps of the inventive method when the program is executed in the control device of the tomography unit. Such a software implementation is advantageous to the extent that it is also possible hereby for already available suitable tomography units to be more easily retrofitted in order to operate using at least one embodiment of the inventive method.

As explained, in order to save an applied dose, the scanning of the movement phases is advantageously carried out such that it is precisely the respectively required signal-to-noise ratio, that is to say the minimum image quality, that is achieved for the tomographic images produced. By way of example the signal-to-noise ratio required or requested in the respective images can be input by means of a keyboard by a user at the beginning of the examination. Alternatively, the signal-to-noise ratios required for the later diagnosis can also be read out automatically, as a function of the selected phases to be displayed, from a database in which, for example, optimum values determined experimentally or by simulation are stored. In particular, it is possible to store these values in scan protocols that respectively include the parameter values required for automatically driving the tomography unit for a specific examination or study.

In at least one embodiment of a method, an initial instant and a final instant are determined prospectively in relation to each of the time windows by taking account of at least one fluctuation parameter, the fluctuation parameter characterizing an irregularity in the periodic movement of the object. As an example, it is possible in this way in the ECG signal for the position of the time window to be estimated prospectively with more reliability with reference to the R-wave of the heart cycle, since the estimate can be adapted dynamically to changes occurring in the cardiac frequency. Changes in the cardiac frequency could be produced, for example, by ergometric loading and by the use of contrast agent, for example by the use of adenosine.

The fluctuation parameter is preferably determined by an analysis of a prescribed number of prior periods of the movement of the object, a trend in the duration of the analyzed periods being very particularly preferred as fluctuation parameter. A corresponding possibility for determining the initial instant and the final instant by using the trend in the duration of the preceding periods within an ECG is disclosed, for example, in DE 10 2005 036 963 B3, the entire contents of which is hereby incorporated herein by reference.

It is also prospectively defined with particular preference and as a function of the period of the movement of the object in which of the two time windows a lower value of the tube current is set, and in which of the two time windows a value of the tube current that is higher in relation thereto is set. Thus, for example, it can depend on the period as to whether it is more advantageous to make an image of higher quality in a first time window, and therefore an image of poorer quality in a second time window, or vice versa. For example, in the case of a cardiac examination the area of the end diastole is generally better in order to produce an image of high quality in which the coronary vessels are displayed in a fashion free from movement. With increasing heart rate, that is to say with a reduction in the ECG, however, the temporal range of the end diastole becomes ever smaller in relation to the area of the end diastole. The reason for this is that the duration of the contraction of the heart is relatively independent of the heart rate. Thus, if the heart rate rises, there is first and foremost a change in the position of the diastole that therefore becomes shorter with rising heart rate.

Consequently, for low heart rates it can be sensible to carry out the recording of higher quality as usual at the instant of the end diastole, that is to say in the second time window, in order to detect the coronary vessels, and to set a higher tube current here. By contrast, for higher heart rates it would be necessary to prepare the higher quality image in the first time window, which acquires at least a portion of the end systole, whereas a lower tube current is then set when recording the end diastole. This way of specifying which tube current is used in which window can be performed automatically. Heart rates below 75 bpm (beats per minute), can be regarded as low heart rates in the case of which the higher quality recording is carried out in the area of the end diastole.

It is sensible not to emit X-radiation before and after the detection of the projections in the desired time windows at the relevant z-position, that is to say during a repositioning of the recording system to a new z-position. However, the tube current is also preferably lowered between the time windows to a value that is below the values of the tube current in the two time windows. A very considerable lowering is advantageously performed in this case. Thus, the value in one of the two time windows is preferably equal to or less than approximately 1/5 of the value in the other time window, and the tube current is preferably lowered between the time windows only to a value equal to or less than approximately 1/20 of the maximum current required in the case of the recording of higher quality. It is particularly preferred, in order to minimize the dose between the two time windows, even to lower the tube current to the value 0.

Since the two time windows can respectively be determined prospectively separately from one another in each case, overlapping of the two time windows can occur in principle. In this case, it should be ensured that the respectively higher value of the tube current is set automatically in the overlap region of the two time windows.

In order to save calculating time, the method can also be carried out in principle such that a preceding time window and a subsequent time window adjoin one another directly within a cycle. That is to say, a first initial instant is then determined for the first window, then a further instant that simultaneously forms the final instant for the first window and the initial instant for the second window, and finally a final instant for the end of the second window.

BRIEF DESCRIPTION OF THE DRAWINGS

The invention is explained in more detail once again below with reference to the attached figures, and with the aid of example embodiments. In the drawing:

FIG. 2 shows a first variant of a time response of a current modulation of the tube current in relation to an ECG signal, FIG. 3 shows a second variant of a time response of a current modulation of the tube current in relation to an ECG signal.

DETAILED DESCRIPTION OF THE EXAMPLE EMBODIMENTS

Figure 1:
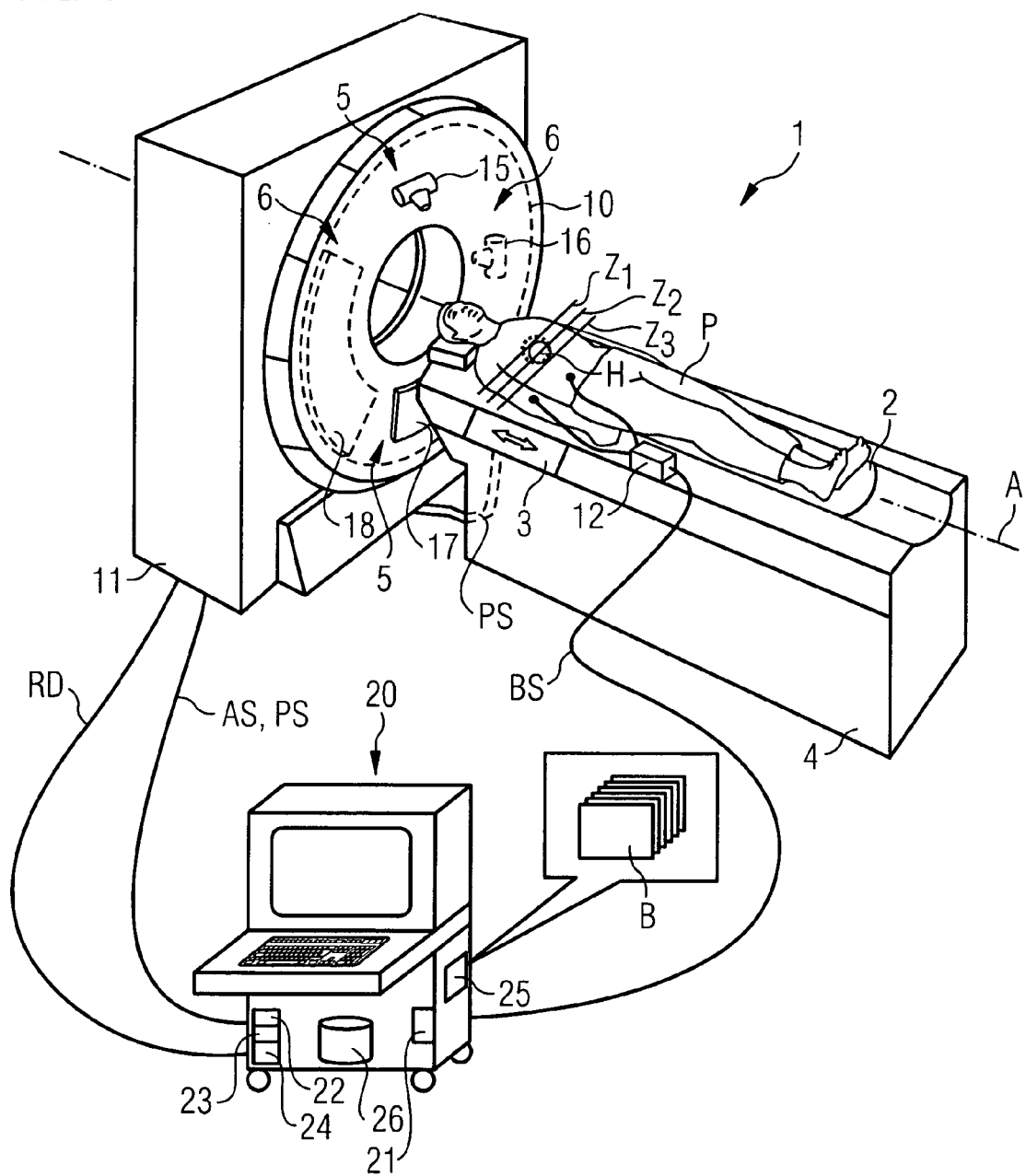
FIG. 1 shows an inventive computed tomography unit in a perspective illustration.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic perspective view of an inventive tomography unit. The tomography unit has in a gantry housing 11 a gantry 10 that can be rotated about a system axis (denoted in general as z-axis A) and has at least one recording system 5 comprising an X-ray emitter 15 and a radially opposite X-ray detector 17. The tomography unit can also optionally have still further recording systems. In FIG. 1, a second recording system 6 is illustrated that is offset by 90° from the first recording system 5 and has a further X-ray tube 16 and a second detector 18. The use of a plurality of recording systems angularly offset from one another has the advantage that recordings can be prepared in a substantially shorter time since a larger angular range is covered at the same time and therefore various projections can be acquired simultaneously. This is advantageous particularly in the case of the recording of quickly moving organs.

Located in the z-direction upstream of the gantry housing 11 is a patient table 2 that can be moved on a base 4, at least in the direction of the z-axis, with the aid of a positioning device 3. It is possible in this way to move a patient P lying on the patient table 2 into the measuring zone inside the gantry 10 of the gantry housing 11, and in the process for the area of the object to be examined, here the heart H of the patient P, for example, to be positioned at the appropriate position in the isocenter of the tomograph. By way of example, the positioning device 3 can be implemented in the usual way by a mechanism driven in a suitable way by electric motors and/or by electrically controllable, pneumatic and/or hydraulic assemblies.

In the example embodiment illustrated in FIG. 1, the patient table 2 is moved into a fixed gantry housing 11, and the patient or the object H to be examined is thereby positioned appropriately in relation to the gantry housing 11.

There are also possible in principle, however, example embodiments in which the gantry housing is displaced and the patient himself lies, for example, on an examination table located in a fixed position. All that is essential is the relative positioning of the examined object H in relation to the recording system 5, 6.

It may be pointed out at this juncture that instead of the example embodiment illustrated it is also possible for the tomography unit to be designed in a completely different form. For example, in most cases the gantry is additionally designed such that it can pivot transverse to the z-axis so as to produce tomographic images lying not only perpendicular to the z-axis, but also obliquely. Likewise, the recording systems can be differently designed. For example, it is possible to use a detector that does not rotate with the X-ray source, but runs annularly around the entire gantry. The precise design of the recording system is largely immaterial for embodiments of the present invention.

The control of the tomography unit is performed with the aid of a control device 20 that is connected to the gantry housing 11 via a suitable control and data lines. Illustrated in FIG. 1 is a control line via which drive signals AS for the recording system, and position control signals PS for the position control 3 of the patient table are transferred, and these in turn are connected to the gantry housing 11 via cables. To this end, the control device 20 has suitable interfaces 22 for driving the recording system 5, 6, and an interface 23 for driving the positioning device 3, which is illustrated here as a common interface 22, 23.

Via a further line, raw data RD that are acquired by the detectors 17, 18 of the recording system are passed onto a raw data interface 24 of the control device 20. It is clear that instead of a raw data line and a drive line it is also possible for a multiplicity of further control and data lines to be present between the control device 20 and gantry housing 11 and also the patient table 2. Likewise, all the lines can also be combined into one line. All interfaces need to be adapted consequentially.

The raw data acquired via the raw data interface 24 are fed to an image computer unit 25 that is here a part of the control device 20 and which reconstructs the desired tomographic images B from the projections acquired with the aid of the detectors 17, 18. Said tomographic images can be displayed at once to the user on a display of the control device 20, and/or be stored in a memory 27. They can also be transferred via an interface (not illustrated) to further components, for example analysis stations, that are connected to the control device via a network, or stored on bulk storage devices connected to this network, or printed out at filming stations or the like.

For actually driving the recording system 5, 6 and the positioning device 3, the control device 20 has a measurement control unit 26 that generates control signals, for example on the basis of scan protocols that are stored in the memory 27 or obtained via a network connection and include the parameters required for the automatic control and are transferred via the interfaces 22, 23 to the relevant components of the tomography unit.

Via a user interface that has, for example, as illustrated here a keyboard, a display and, if appropriate, also further input means such as a mouse or the like, a user can also select the suitable scan protocols and, if appropriate, change them in order thus finally to prescribe the measurement.

As is to be seen in FIG. 1, the patient P is connected in the usual way to an electrocardiogram unit 12 by means of electrodes (of which here only two are illustrated schematically). An ECG signal BS thereby simultaneously acquired during the recording of the tomographic images B is transferred to a movement signal interface 21 of the control device 20 as movement signal BS. It can be used there in order to drive the tomography unit 1 in the way subsequently described in a fashion triggered by the ECG signal BS, and thus to produce in an inventive way recordings of the cyclically moving heart H of the patient P in completely specific movement phases. The movement signal BS is preferably transferred in digital form from the electrocardiogram unit 12. Alternatively, it is also possible for the movement signal interface 21 to have a digital/analog converter in order to convert an analog movement signal into digital data and then to use the latter in the measurement control unit 26.

Both the measurement control unit 26 and the image computer unit 25 as well as, if appropriate, a multiplicity of further components (not illustrated) in the control device 20 are preferably implemented in the control device 20, preferably in the form of software modules on one or, if appropriate, more interlinked processors.

In the example embodiment illustrated, a typical case is illustrated in which the width of the detectors 17, 18 in the z-direction does not suffice in order to immediately acquire projections of the complete heart H along the z-direction. Consequently, it is necessary to prepare projections one after another at various z-positions, of which here three z-positions $z_1$, $z_2$, $z_3$ are depicted by way of example, in order to obtain an image of a complete heart.

As set forth at the beginning, the problem resides in that in order to display a specific movement phase all the projections must originate from this movement phase. This would be possible by preparing simple projections of the complete movement cycle of the heart in all z-positions, and retrospectively using only the projections that are recorded in the appropriate phases in order to produce the desired images with the aid of the ECG signal recorded. However, for the patient this means a relatively high X-ray exposure that should be avoided. Therefore, the system operates in the inventive way in order to acquire computed tomography images in a plurality of movement phases in the inventive way by defining suitable windows for the individual movement phases of interest, and by defining an X-ray dose required precisely for the respective movement phase in order to produce a useful image, and the tube current to be prescribed for the purpose.

FIG. 2 shows a variant for a preferably adjustable time response of the current modulation of the tube current I in relation to the ECG signal BS of the patient P against the time t in accordance with an example embodiment of the invention. In this case, tomographic images of different image quality are produced by appropriate modulation of the tube current I in a first time window $F_1$ in a first movement phase $P_1$ (that is to say, the time window $F_1$ covers at least a part of the first movement phase $P_1$) and in a second time window $F_2$ in a second movement phase $P_2$ (that is to say, the time window $F_2$ covers at least a part of the second movement phase $P_2$) of the heart H. The lower part of the figure in this case illustrates a typical ECG signal BS in which the movement phases $P_1$, $P_2$ are defined. Such an ECG signal BS exhibits a so-called R-wave R as a particularly characteristic feature for each heartbeat. An R-wave is particularly suitable for triggering control of the tomography unit. What is involved here in the case of the first movement phase $P_1$ is the so-called end systole in which the heart is contracted. The second movement phase $P_2$ is here the end diastole, in which the heart is expanded, that is to say filled with blood. In the diagram depicted there-above, the X-ray tube current I is plotting against the time t. It may be pointed out at this juncture that the modulation is illustrated here as a very sharp rectangular modulation. In reality, such rectangles generally cannot be achieved, but rather, it is necessary to accept relatively long rise and fall times.

One of the time windows $F_2$ would suffice for a single recording for the purpose of reproducing the coronary vessels of the heart in a fashion free from movement. As a rule, use is made for this purpose of the end diastole $P_2$, since the latter generally lasts longer and it is therefore possible to select a somewhat larger time window in order to acquire the desired projections in a fashion free from movement.

However, it is also necessary to record in the phase of maximum contraction for a functional imaging of the heart. In the tomographic images produced therefrom, it is necessary only to determine the size of the ventricle in order then to compare the latter with the size of the ventricle obtained from the recorded tomographic images produced at the instant of the end diastole. The ejection fraction can be determined therefrom. By contrast with a recording that is intended to provide information on the state of the coronary vessels, there is no need for a particularly good recording quality in order to determine the size of the ventricle, since the chamber wall can be effectively detected even in images with relatively high image noise. Thus, in order to keep the overall X-ray dose as low as possible, in the case of the method in accordance with FIG. 2 the windows $F_1$, $F_2$ are firstly defined for the end systole $P_1$ and the end diastole $P_2$, for which purpose the initial instants $t_1$, $t_3$ and a final instants $t_2$, $t_4$ of the time windows $F_1$, $F_2$ are prospectively determined.

These instants $t_1$, $t_2$, $t_3$, $t_4$ are defined here prospectively with reference to the preceding R-wave R in the ECG signal BS on the basis of an evaluation of at least the preceding period of the cardiac cycle, that is to say by making an estimate. However, in order to improve the estimate it is preferred to determine a trend in the change in the period by an evaluation of a plurality of periods recorded in the past, and then to take account of this trend. When estimating, it is additionally possible also to take account of further fluctuation parameters, such as the spread of the period, in addition to the trend. It is preferred to use all easily available parameters with the aid of which changes in the periods can be mathematically described. The optimization of the phase angle of the end systole $P_1$ is typically between 30% and 40% of the RR cycle of the ECG signal, whereas the end diastole $P_2$ is often to be found between 60% and 70% of the RR cycle. DE 10 2005 036 963 B3 describes a large variety of methods that can be used to take account of such parameters.

The tube current values $I_1$, $I_2$ actually required in the associated movement phases $P_1$, $P_2$ for the quality of the images that is to be achieved are now defined for each of the windows $F_1$, $F_2$. In the example embodiment illustrated in FIG. 1, a relatively low current $I_1$ of approximately 100 mA is prescribed for measuring the projections of the end diastole. By contrast, a substantially higher current $I_2$ of approximately 500 mA is prescribed for measuring the projections in the time window $F_2$ for the end diastole $P_2$, since the aim here is to achieve a better signal-to-noise ratio.

In the course of the recording method, the positioning device 3 is then driven such that firstly the heart is positioned in a first z-position $z_1$ relative to the recording system. That is to say, the patient P is positioned such that the line of intersection depicted in FIG. 1 relative to the heart H and denoted as z-position $z_1$ lies in the isocenter of the gantry 10, in order to produce the desired recording of the tomographic image there. After the correct positioning of the recording systems 5, 6 at the location $z_1$ has taken place, the projections are acquired with the aid of the prescribed tube currents $I_1$ and $I_2$ respectively, in a fashion fitting the ECG signal at the time windows $F_1$, $F_2$ illustrated in FIG. 2.

In the example shown, the heart is beating with a frequency of 60 bpm. In order to reconstruct a tomographic image that images a movement phase $P_1$, $P_2$, it is necessary to acquire sufficient projections such that measured data for parallel projections over an angular interval of at least 180 degrees. In the case of the scanning geometry of a computer tomography unit shown in FIG. 1, this is generally the case when an angular range of 180 degrees plus fan angle is swept by the recording system. The rate of rotation of the gantry is generally selected such that the projections required for reconstructing a tomographic image could be acquired with a recording system in a time window of typically less than 250 ms. In the case of the illustrated computer tomography unit having two recording systems, the required time interval is halved such that all the required projections in a cardiac cycle can be acquired even in the case of high cardiac frequencies.

Should the cardiac frequency become so high that it is impossible to record projections belonging to a complete reconstruction interval during a single cardiac cycle, this can be performed during the phase of a number of consecutive cardiac cycles that is to be recorded, the recording system remaining stationary for so long at the respective z-position. The reconstruction interval is then composed of a number of data intervals belonging to different cardiac cycles. This procedure is known as multi-segment reconstruction.

If all desired projections have been recorded at a z-position $z_1$, it is then possible to drive the positioning device 3 such that the next z-position $z_2$ is approached, said z-position $z_2$ preferably lying such that areas acquired by the recording system 5, 6 seamlessly border one another in the z-direction in the area acquired at the position $z_1$, or at most overlap one another slightly such that the heart can be acquired without a gap. The required projections are then produced there.

Subsequently, the further positions are approached sequentially, and the projections are also prepared in the two time windows $F_1$, $F_2$ in accordance with an embodiment of the inventive method. For the sake of simplicity, only three z-positions $z_1$, $z_2$, $z_3$ are depicted in FIG. 1. It is clear that in reality it is mostly a multiplicity of further z-positions that are approached. This depends in the final analysis on the width of the detectors and on the extent in the z-direction of the relevant objects to be examined.

It is illustrated in FIG. 2 that the tube current sinks to 0 within the RR cycle between the two time windows $F_1$, $F_2$ in order to emit a minimum X-ray dose. During a repositioning within the sequential measuring process, that is to say before the measurement in the first time window $F_1$ and after the measurement in the last time window $F_2$ at a specific z-position, the X-ray tube should be set in any case such that no X-ray dose is administered.

FIG. 3 shows a variant in which, however, the drop between the time windows (and, if appropriate, also before the first time window $F_1$ and after the last time window $F_2$, it being necessary, however, for the object already to be in the respectively appropriate z-position) is measured further with a very low tube current $I_3$. This tube current can be 5% of the higher tube current $I_2$, for example. This variant would be used whenever in a special case it is further required to have image information outside the individual defined windows for further analyses, but the price of this is a higher dose.

It is illustrated in FIGS. 2 to 5 that the X-ray tube is operated in the second time window $F_2$ with a higher current $I_2$ in the area of the end diastole $P_2$ in order to produce an image of better quality. This need not necessarily be so. As a rule, the end diastole is certainly used to produce the images of better quality for the purpose of observing the coronary vessels. However, in the case of relatively high heart rates it can also be sensible to prepare the image of higher quality in the movement phase $P_1$ of the end diastole, since with rising heart rate the movement phase $P_2$ of the end diastole becomes ever shorter relative to the movement phase $P_1$ of the end systole. In accordance with a preferred design of the invention, the measurement control unit can operate to this end such that above a, for example, adjustable cardiac frequency the tube current level for the first time window $F_1$ is automatically set in the area of the end systole $P_1$ to a higher value and, contrarily, the tube current level is automatically set in the area of the end diastole $P_2$ to the lower value $I_1$ in the second time window $F_2$.

Figure 4:
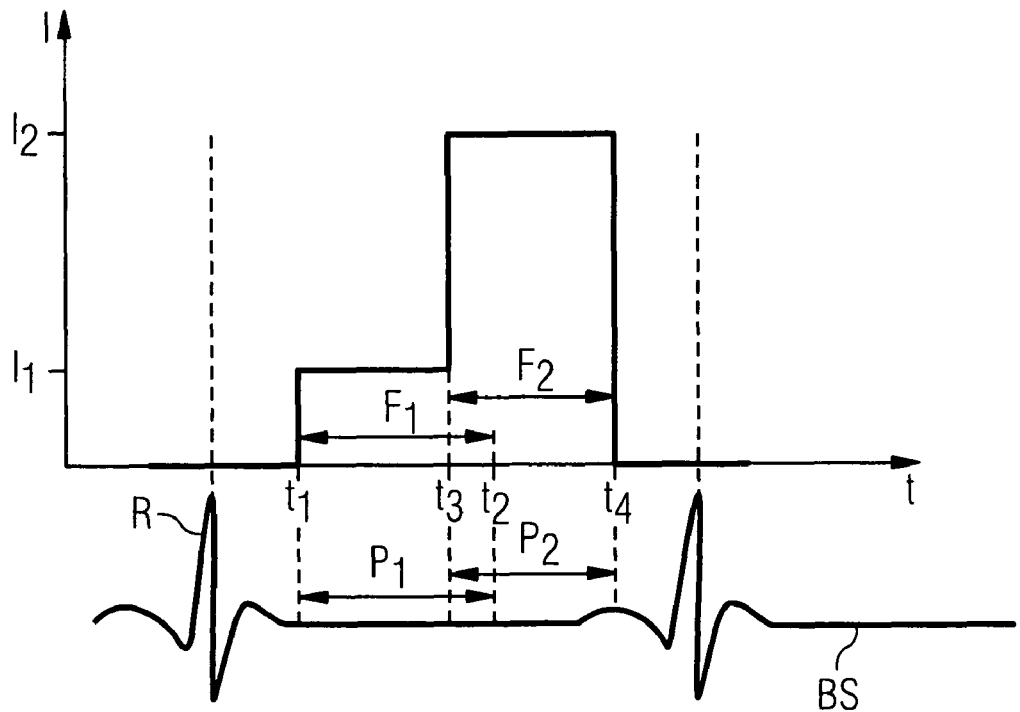
FIG. 4 shows a third variant of a time response of a current modulation of the tube current in relation to an ECG signal.

Since the cardiac frequency or the shape of the movement signal or, in particular, the length of the individual phases can change drastically, and the respective initial instants $t_1$, $t_3$ of the time windows $F_1$, $F_2$ and also the final instants $t_2$, $t_4$ can be prospectively determined separately taking account of the mentioned fluctuation parameters, it can happen that the final instant $t_2$ of the first window $F_1$ lies after the prospectively determined initial instant $t_3$ of the second window $F_2$. In this case, the windows $F_1$, $F_2$ overlap one another, as is illustrated in FIG. 4. In order in any case to ensure that for the phase for which an image of higher quality is required the associated time window in which the high tube current required should be present is wide enough, it is preferably ensured in the event of overlapping of the windows that the higher current level $I_2$ takes precedence in the overlap region in the way shown in FIG. 4.

Figure 5:
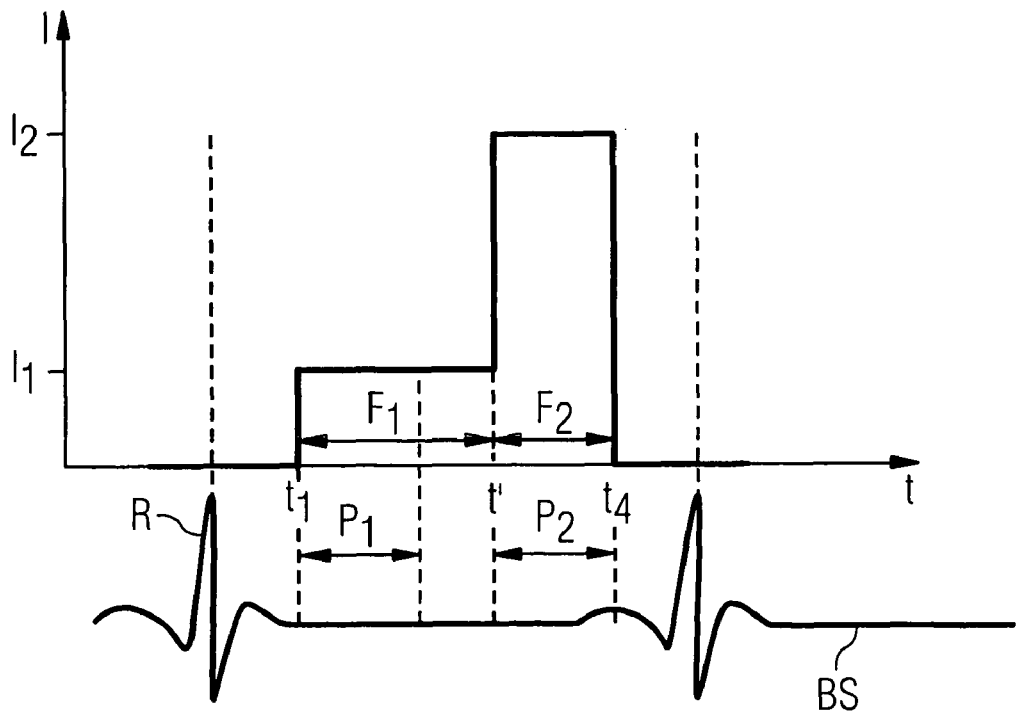
FIG. 5 shows a fourth variant of a time response to a current modulation of the tube current in relation to an ECG signal.

FIG. 5 shows a further example embodiment, in which the computational outlay for determining the time windows $F_1$, $F_2$ has been simplified somewhat. Here, the final instant $t_2$ for the first time window has been combined with the initial instant $t_3$ for the second time window $F_2$ to form a common limiting instant t' that is at the same time the final instant of the first time window and initial instant of the second time window. That is to say, the windows $F_1$ and $F_2$ therefore always border one another directly. The advantage consists in that four instants need no longer be prospectively determined, but only just three. However, even this variant is associated with a dose that is increased compared with the variant of FIG. 1, and so this variant is sensible when, for example, the heart rate is so high that two separately determined windows $F_1$, $F_2$ lie very closely against one another in any case, or overlap one another.

In the case of the example embodiment illustrated in FIG. 5, it would be sensible to ensure by analogy with the example embodiment in FIG. 4 that the common limiting instant t' is always determined such that the step profile is dominated by the time window in which the higher current value is to be set, that is to say in which the images of better quality are to be produced. In the case of the example embodiment illustrated in FIG. 5, where the higher current is set in the time window $F_2$, it would thus be necessary to select the limiting instant t' in accordance with the initial instant $t_3$ of the second time window $F_2$. In a converse case, in which the higher current is to be set in the window $F_1$, it would be necessary to select the common limiting instant in accordance with the final instant of the first window.

It may be pointed out once again at this juncture that the previously described designs are only example embodiments, and that the basic principle of decoupling can also be varied widely by a person skilled in the art without departing from the field of the invention, to the extent it is prescribed by the claims. In particular, this method is suitable for producing tomographic images of more than two movement phases. The modulation of the tube current is then performed appropriately such that a specific tube current value is reached in each time window. The invention is, in particular, also not limited to the applications in the case of the production of images of the heart, but can be used in principle for all cyclically moving objects, that is to say other organs or else inanimate technical objects in the field of materials testing.

For the sake of completeness, it may also be pointed out that the use of the indefinite article "a/an" does not exclude the possibility of the relevant features also being present more than once. Likewise, the term "unit" does not preclude the latter from consisting of a plurality of components that can also be distributed in space, if appropriate.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing tomographic images, relating to different movement phases of a periodically moving object, via a tomography unit including at least one recording system arranged rotatably about a z-axis of the tomography unit, the at least one recording system including an X-ray tube to which a tube current is applicable and a detector to acquire projections, the method comprising:

positioning the at least one recording system relative to the object at a first z-position along the z-axis;

acquiring projections from a multiplicity of different projection directions at the first z-position in a fashion triggered by a movement signal representing movement of the object, projections relating to a first movement phase of the object being acquired in a prospectively defined first time window and projections relating to at least a second movement phase of the object being acquired in a prospectively defined second time window, the first movement phase and the second movement phase being in a same cycle of the object, an initial instant and a final instant relating to each of the time windows are prospectively determined taking account of at least one fluctuation parameter, the at least one fluctuation parameter characterizing an irregularity of the periodic movement of the object and a modulation of the tube current being performed in such a way that different values of the tube current are set in the first and the at least second time window to attain a prescribable different signal-to-noise ratio in produced images;

sequentially positioning the recording system and respectively acquiring projections for at least the first and second movement phases in accordance with the positioning and acquiring steps at further z-positions along the z-axis until a prescribed examination area is scanned at the desired z-positions; and reconstructing, in real time or subsequent reconstruction, tomographic images on the basis of the acquired projections.

2. The method as claimed in claim 1, wherein the at least one fluctuation parameter is determined by an analysis of a prescribed number of prior periods of the movement of the object.

3. The method as claimed in claim 2, wherein a trend of the period duration of the analyzed periods is used as fluctuation parameter.

4. The method as claimed in claim 1, wherein, as a function of an expected period duration of the movement of the object, it is established in which of the two time windows a relatively lower value of the tube current is set, and in which of the two time windows a value of the tube current is set that is relatively higher in relation thereto.

5. The method as claimed in claim 4, wherein, between the time windows, the tube current is lowered to a value that is below the values of the tube current in the two time windows.

6. The method as claimed in claim 5, wherein the tube current is lowered to the value zero between the two time windows.

7. The method as claimed in claim 6, wherein, when the prospectively determined time windows overlap, the respectively relatively higher value of the tube current is set in an overlap region of the two time windows.

8. The method as claimed in claim 1, wherein, between the time windows, the tube current is lowered to a value that is below the values of the tube current in the two time windows.

9. The method as claimed in claim 8, wherein the tube current is lowered to the value zero between the two time windows.

10. The method as claimed in claim 9, wherein, when the prospectively determined time windows overlap, the respectively relatively higher value of the tube current is set in an overlap region of the two time windows.

11. The method as claimed in claim 1, wherein, when the prospectively determined time windows overlap, the respectively relatively higher value of the tube current is set in an overlap region of the two time windows.

12. The method as claimed in claim 1, wherein the object is a heart of a patient or test subject.

13. The method as claimed in claim 12, wherein the first movement phase relates to the end diastole, and the second movement phase relates to the end systole.

14. The method as claimed in claim 1, wherein the movement signal is an ECG signal of a patient or test subject.

15. A control device for a tomography unit, the tomography unit including at least one recording system arranged rotatably about a z-axis of a tomography unit, the at least one recording unit including an X-ray tube to which a tube current is applicable and a detector to acquire projections, as the tomography device further including a positioning device to position the at least one recording system relative to an object to be examined at prescribed z-positions along the z-axis, the control device comprising:

a movement signal interface to acquire a movement signal representing movement of the object;

an interface to drive the at least one recording system; and an interface, to drive the positioning device, designed such that in order to produce tomographic images relating to different movement phases of a periodically moving object, wherein the at least one recording system is positioned relative to the object at a first z-position along the z-axis, projections are acquired from a multiplicity of different projection directions at this first z-position, in a fashion triggered by the movement signal, projections relating to a first movement phase of the object being acquired in a prospectively defined first time window and projections relating to at least a second movement phase of the object being acquired in a prospectively defined second time window, the first movement phase and the second movement phase being in a same cycle of the object, an initial instant and a final instant relating to each of the time windows are prospectively determined taking account of at least one fluctuation parameter, the at least one fluctuation parameter characterizing an irregularity of the periodic movement of the object and a modulation of the tube current being performed such that different values of the tube current are set in the first and the second time window in order to attain a prescribable different signal-to-noise ratio in the produced images, and the at least one recording system is sequentially positioned at further z-positions along the z-axis relative to the object at the first z-position along the z-axis, and projections for at least the two movement phases are acquired at the z-positions from a multiplicity of different projection directions at the first z-position until a prescribed examination area is scanned at the desired z-positions.

16. A tomography unit comprising:

at least one recording system, arranged rotatably about a z-axis of the tomography unit, including an X-ray tube to which a tube current is applicable, and a detector to acquire projections;

a positioning device to position the at least one recording system relative to an object to be examined at prescribed z-positions along the z-axis;

a control device as claimed in claim 15; and an image computer unit, designed to construct graphic images in a real time fashion or subsequently on the basis of the acquired projections.

17. A computer program product, loadable directly into a memory of a programmable control device of a tomography unit, comprising program code portions, in order to execute all the method as claimed in claim 1 when the program is executed in the control device of the tomography unit.

18. A non-transitory computer readable medium including program segments for, when executed on a programmable control device of a tomography unit, causing the programmable control device to implement the method of claim 1.

* * * * *